(12) United States Patent
Hansen et al.

(10) Patent No.: US 8,789,532 B2
(45) Date of Patent: Jul. 29, 2014

(54) VENTILATION MASK

(75) Inventors: Norman Hansen, Highland Beach, FL (US); Louis Javier Collazo, Atlanta, GA (US); Sanjay Chandran, Boca Raton, FL (US)

(73) Assignee: Respcare, Inc., Coconut Creek, FL (US)

( * ) Notice: Subject to any disclaimer, the term of this patent is extended or adjusted under 35 U.S.C. 154(b) by 1342 days.

(21) Appl. No.: 11/372,025

(22) Filed: Mar. 10, 2006

(65) Prior Publication Data

US 2007/0221226 A1    Sep. 27, 2007

(51) Int. Cl.
*A62B 18/02* (2006.01)

(52) U.S. Cl.
USPC ............. 128/206.21; 128/206.24; 128/206.26

(58) Field of Classification Search
USPC ............. 128/207.13, 205.25, 206.18, 206.27, 128/206.23, 206.24, 206.21, 207.11, 128/202.27, 206.26, 206.28, 207.17
See application file for complete search history.

(56) References Cited

U.S. PATENT DOCUMENTS

| | | |
|---|---|---|
| 1,125,542 A | 1/1915 | Humphries |
| 3,670,726 A | 6/1972 | Mahon et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 4,156,426 A | 5/1979 | Gold |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,422,456 A | 12/1983 | Teip |
| 4,493,614 A | 1/1985 | Chu et al. |
| 4,549,542 A | 10/1985 | Chien |
| 4,587,967 A | 5/1986 | Chu et al. |
| 4,601,465 A | 7/1986 | Roy |
| 4,617,637 A | 10/1986 | Chu et al. |
| 4,660,555 A | 4/1987 | Payton |
| 4,699,139 A | 10/1987 | Marshall et al. |
| 4,706,664 A | 11/1987 | Snook et al. |
| 4,739,755 A * | 4/1988 | White et al. ............. 128/206.12 |

(Continued)

FOREIGN PATENT DOCUMENTS

| | | |
|---|---|---|
| DE | 146688 | 2/1981 |
| DE | 19944242 | 3/1991 |

(Continued)

OTHER PUBLICATIONS

Respironics Co.—Mask Family—http://masksfamily.respironics.com/ viewed on Jul. 24, 2006.

(Continued)

*Primary Examiner* — Steven Douglas
(74) *Attorney, Agent, or Firm* — Maier & Maier, PLLC

(57) ABSTRACT

A ventilation mask having a cushioned facial interface and an adjustable support structure. The ventilation mask can have a gas delivery port with a gas delivery tube rotatably coupled thereto. The cushioned facial interface may have one or more interior membranes and an extended lower portion. The support structure may have an adjustable slide allowing a wearer to adjust the mask to increase comfort while maintaining a gas-tight seal between the mask and the face of the wearer.

29 Claims, 8 Drawing Sheets

(56) References Cited

U.S. PATENT DOCUMENTS

| | | | |
|---|---|---|---|
| 4,753,233 A | 6/1988 | Grimes | |
| 4,774,946 A | 10/1988 | Ackerman et al. | |
| 4,899,740 A | 2/1990 | Napolitano | |
| 4,915,105 A | 4/1990 | Lee | |
| 4,996,983 A | 3/1991 | AmRhein | |
| 5,000,173 A | 3/1991 | Zalkin et al. | |
| 5,022,900 A | 6/1991 | Bar-Yona et al. | |
| 5,025,805 A | 6/1991 | Nutter | |
| 5,038,772 A | 8/1991 | Kolbe et al. | |
| 5,046,491 A | 9/1991 | Derrick | |
| 5,074,297 A * | 12/1991 | Venegas | 128/204.18 |
| 5,113,857 A | 5/1992 | Dickerman et al. | |
| 5,121,745 A | 6/1992 | Israel | |
| 5,127,397 A | 7/1992 | Kohnke | |
| 5,137,017 A | 8/1992 | Salter | |
| D333,015 S * | 2/1993 | Farmer et al. | D24/110.4 |
| 5,188,101 A | 2/1993 | Tumolo | |
| 5,265,592 A | 11/1993 | Beaussant | |
| 5,265,595 A | 11/1993 | Rudolph | |
| 5,269,296 A | 12/1993 | Landis | |
| 5,271,391 A | 12/1993 | Graves | |
| 5,299,599 A | 4/1994 | Farmer et al. | |
| 5,335,656 A | 8/1994 | Bowe et al. | |
| 5,355,893 A | 10/1994 | Mick et al. | |
| 5,372,130 A * | 12/1994 | Stern et al. | 128/205.25 |
| 5,375,593 A | 12/1994 | Press | |
| 5,385,141 A | 1/1995 | Granatiero | |
| 5,394,568 A | 3/1995 | Brostrom et al. | |
| 5,396,885 A | 3/1995 | Nelson | |
| 5,398,676 A | 3/1995 | Press et al. | |
| 5,400,776 A | 3/1995 | Bartholomew | |
| 5,419,318 A * | 5/1995 | Tayebi | 128/205.27 |
| 5,425,359 A | 6/1995 | Liou | |
| 5,437,267 A | 8/1995 | Weinstein et al. | |
| 5,509,409 A | 4/1996 | Weatherholt | |
| 5,526,806 A | 6/1996 | Sansoni | |
| 5,533,506 A | 7/1996 | Wood | |
| 5,540,223 A * | 7/1996 | Starr et al. | 128/205.25 |
| 5,560,354 A | 10/1996 | Berthon-Jones et al. | |
| 5,682,881 A | 11/1997 | Winthrop et al. | |
| 5,740,799 A | 4/1998 | Nielsen | |
| 5,794,619 A | 8/1998 | Edelman et al. | |
| 5,906,203 A | 5/1999 | Klockseth et al. | |
| 5,954,049 A | 9/1999 | Foley et al. | |
| 6,102,040 A * | 8/2000 | Tayebi et al. | 128/206.24 |
| 6,123,071 A | 9/2000 | Berthon-Jones et al. | |
| 6,357,441 B1 | 3/2002 | Kwok et al. | |
| 6,431,172 B1 | 8/2002 | Bordewick | |
| 6,439,234 B1 | 8/2002 | Curti et al. | |
| 6,478,026 B1 | 11/2002 | Wood | |
| 6,561,188 B1 | 5/2003 | Ellis | |
| 6,561,193 B1 | 5/2003 | Noble | |
| 6,571,798 B1 | 6/2003 | Thornton | |
| 6,581,602 B2 | 6/2003 | Kwok et al. | |
| 6,595,214 B1 | 7/2003 | Hecker et al. | |
| 6,595,215 B2 | 7/2003 | Wood | |
| 6,637,434 B2 | 10/2003 | Noble | |
| 6,655,385 B1 | 12/2003 | Curti et al. | |
| 6,679,265 B2 | 1/2004 | Strickland et al. | |
| 6,763,831 B2 * | 7/2004 | Sniadach | 128/206.29 |
| 6,766,800 B2 | 7/2004 | Chu et al. | |
| 7,069,932 B2 * | 7/2006 | Eaton et al. | 128/206.24 |
| 7,406,965 B2 * | 8/2008 | Kwok et al. | 128/206.21 |
| 8,136,523 B2 * | 3/2012 | Rudolph | 128/206.24 |
| 2002/0046755 A1 | 4/2002 | DeVoss | |
| 2002/0124849 A1 | 9/2002 | Billette de Villemeur | |
| 2003/0079749 A1 | 5/2003 | Strickland et al. | |
| 2003/0196658 A1 | 10/2003 | Ging et al. | |
| 2004/0079375 A1 * | 4/2004 | Lithgow et al. | 128/206.21 |
| 2004/0112384 A1 | 6/2004 | Lithgow et al. | |
| 2004/0118406 A1 * | 6/2004 | Lithgow et al. | 128/206.24 |
| 2004/0226563 A1 * | 11/2004 | Xu et al. | 128/206.21 |
| 2005/0028822 A1 | 2/2005 | Sleeper et al. | |
| 2005/0033247 A1 | 2/2005 | Thompson | |
| 2005/0051176 A1 | 3/2005 | Riggins | |
| 2005/0061326 A1 | 3/2005 | Payne, Jr. | |
| 2006/0076019 A1 * | 4/2006 | Ho | 128/206.24 |

FOREIGN PATENT DOCUMENTS

| | | |
|---|---|---|
| DE | 3719009 | 12/1998 |
| EP | 0658356 | 6/1995 |
| GB | 0532214 | 1/1941 |
| GB | 2368533 | 5/2002 |
| WO | WO 01/97892 A1 | 12/2001 |
| WO | PCT/AU2004/001832 | 7/2005 |

OTHER PUBLICATIONS

ResMed Co.—Mask Products—http://resmed.com/portal/site/ResMedUS/index.jsp?_front door=true viewed on Jul. 24, 2006.

Fisher and Paykel Co.—Product Family—http://www.fphcare.com/osa/products.asp viewed on Jul. 24, 2006.

Hans Rudoply Inc.—Mask Products—http://www.rudolphkc.com/products.php?category=MASKS viewed on Jul. 24, 2006.

Snapp Nasal Interface, Tiara Medical Systems, Inc. http://www.tiaramed.com/asp_shop/shopdisplayproducts.asp?id=109 &cat=SNAPP%2A+Nasal+Interface viewed on Jul. 24, 2006.

* cited by examiner

VENTILATION MASK

FIELD OF THE INVENTION

This invention relates to the field of ventilation interfaces and, more particularly, to masks used to treat respiratory ailments.

BACKGROUND

Masks are commonly used in a variety of situations where a user may have trouble breathing. These situations include supplying breathable gas in situations where the ambient level of breathable gas is low, such as in high altitude situations or fire fighting applications. Additionally, these masks may be used to treat a variety of ailments, for example obstructive sleep apnea. The masks typically cover the mouth and nose of a user and have an outer portion that contacts and seals against the face of the user. The delivery of breathable gas in the form of continuous positive airway pressure (CPAP), bilevel positive airway pressure (BiPAP) or variable airway pressure may then be administered to treat the condition of the user.

The masks are typically formed out of a solid material and can include a variety of ports or holes to allow for the delivery of breathable gas and the elimination of exhaust gas. The masks may also have formed on their bodies a variety of flanges or eyelets so as to allow for the fitment of straps, headgear or a harness to secure the mask to the face of a user. Additionally, the masks can utilize a cushion along their outside perimeter. The cushion typically acts to seal the mask against the face of a user, allowing for the proper delivery of input gas and preventing the delivered gas from escaping the mask. The cushion should also, however, be comfortable on the face of the wearer.

These masks often have a variety of problems, however. The masks are frequently formed in such a way that impinges on the comfort of the user. In an effort to create a gas-tight seal of the mask against the face of a wearer, uncomfortable cushions are utilized or the mask must be secured to the head of a wearer in such a fashion that impinges on comfort. Conversely, other masks utilize cushions that do not properly seal the mask against the face of a wearer or do not provide adequate means to secure the mask to the head of a wearer. Frequently the methods employed to secure the mask to the face of a wearer are uncomfortable and do not allow for adequate adjustments that allow a wearer to properly adjust and tailor the fitment of a mask so as to ensure the maximum sealing and comfort levels for that particular wearer. These problems are prominent when a primary purpose of the mask is that it is to be worn for long periods of time, for example, while a user sleeps. Masks that are uncomfortable can lead to a wearer not getting restful sleep, dislodging of the mask while a user sleeps or a user choosing not to wear the mask due to the level of discomfort. Masks that do not seal properly are unable to provide the desired treatment to a wearer.

The cushions on previous masks may also not be tailored to properly provide for sealing and comfort. Cushions are typically formed in a triangular shape, similar to the mask itself. This shape, however, is designed more to follow the contours of the mask rather than adhere to the contours of the face of a wearer. Previous masks also do not have adequate support for the chin of a wearer, which may lead to discomfort and improper sealing. Additionally, cushions used with previous masks have used two or more internal membranes the run throughout the internal perimeter of the cushion. These membranes, however, do not always properly adjust to the size and shape of the mask and therefore prevent proper sealing. Additionally, the use of multiple membranes throughout the internal perimeter of the cushion can distort other portions of the membrane, thereby preventing proper sealing of the cushion against the face of a wearer and impinging on the comfort of the wearer.

A variety of other types of ventilation devices exist that attempt to deliver breathable gas to a wearer while maintaining a seal against the face of a wearer while maintaining user comfort. One example is shown in U.S. Pat. No. 6,581,602 to Kwok, et al. This arrangement shows a cushioned ventilation mask that has fixed flanges, arms and eyelets onto which mounting straps or a harness may be connected. The flanges, arms and eyelets on the mask are not adjustable, however, and therefore can not act to adequately secure the ventilation mask to the face of a wearer while maintaining the highest level of comfort of the wearer.

Another example of a ventilation mask is shown in U.S. Pat. No. 5,647,357. This mask is also cushioned and has several fixed flanges that do not allow for a user to adjust the mask itself while fitting it to their face.

Therefore a need exists for a mask that has adjustability to allow for the proper sealing of the mask against the face of a wearer while maintaining a level of comfort that allows a wearer to use the mask for extended periods of time, for example, while sleeping.

SUMMARY

In one embodiment, a ventilation mask is described. The ventilation mask may have an outer body, a gas delivery tube, a gas delivery port, a cushioned facial interface, a support structure and an adjustable slide. The gas delivery tube may be rotatably connected to the outer body at the gas delivery port. This connection may create a seal between the gas delivery tube and the gas delivery port. The cushioned facial interface may also be removably connected to the outer body and may create a seal between the cushioned facial interface and the outer body. Further, an adjustable slide may be connected to the support structure and may provide additional support and comfort.

In another embodiment, a ventilation mask with an outer body is disclosed. The outer body may include at least one gas entry port that may be connected to a source of breathable gas. Also, a cushion may be connected to the mask, and can form a gas-tight seal with the mask. Further, the cushion may have at least one membrane and may have an extended bottom portion. Additionally, the mask may have an upper portion adjustably secured to the outer body and having a cushion.

In yet another embodiment, a cushion for a ventilation mask is disclosed. The cushion may have a first side having a first and second membrane, a second side having a first and second membrane, a top portion having a first membrane and a bottom portion having a first membrane. The first side, second side, top portion and bottom portion may form a gas tight seal between the cushion and a ventilation mask. Additionally, the bottom portion may extend outwards from the cushion and may provide support for the ventilation mask.

BRIEF DESCRIPTION OF THE DRAWINGS

Advantages of embodiments of the present invention will be apparent from the following detailed description of the preferred embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Generally referring to FIGS. 1-7, a ventilation mask is shown. The mask may fit over the mouth and nose of a user and provide a gas-tight seal against the face of a user. The mask may have a variety of ports or holes for the delivery of breathable gas as well as the removal of exhaust gas. The mask may also have one or more adjustable or deformable slides, arms, members, flanges or eyelets, allowing for a user to adjust the shape and fitment of the mask in order to better provide a gas-tight seal of the mask against the face of a user as well as allowing for a user to increase their level of comfort while wearing the mask.

Figure 1:
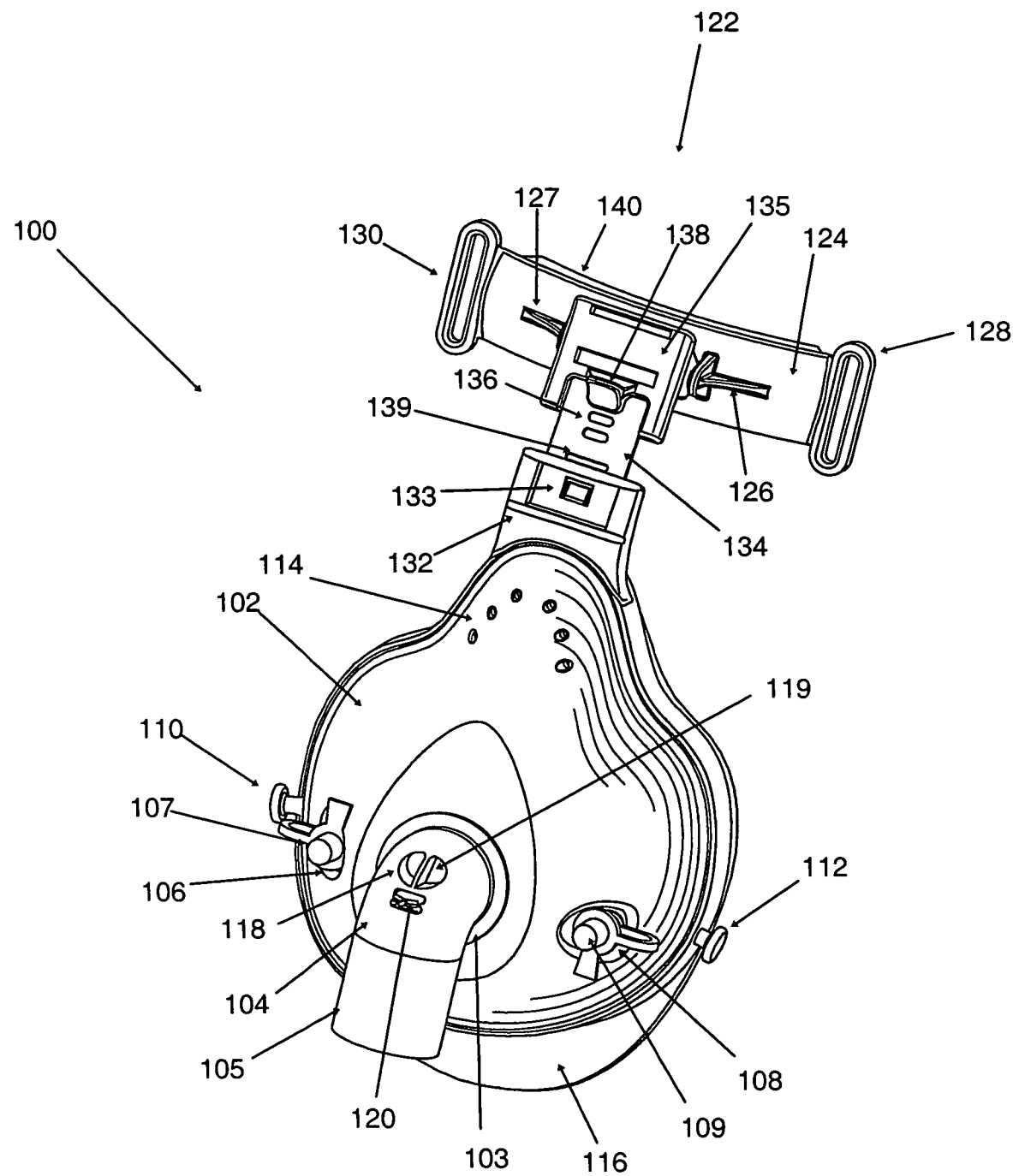
FIG. 1 shows an exemplary rotated perspective view of a ventilation mask.

An exemplary side perspective view of a ventilation mask is shown in FIG. 1. In this embodiment, ventilation mask 100 has a variety of components to properly deliver breathable gas while maintaining a comfortable seal against the face of a wearer. Mask 100 may have outer body 102. In one exemplary embodiment, outer body 102 may be formed out of plastic. Alternatively, outer body 102 may be formed out of any other suitable material known by one of ordinary skill in the art. Outer body 102 may also have port 103 which allows for the insertion of delivery tube 104. Delivery tube 104 may be inserted into port 103 and coupled so as to provide a gas-tight seal between outer body 102 and delivery tube 104. Delivery tube 104 may be formed out of any appropriate material, for example plastic, and may have any shape, for example an elbow shape. The coupling between outer body 102 and delivery tube 104 may be made in any of a variety of manners, for example snapping delivery tube 104 into port 103, having a receiving flange disposed in port 103 that accepts delivery tube 104, or having threading in port 103 that may allow for delivery tube 104 to be screwed into the port. Other methods of connecting delivery tube 104 to outer body 102 may include using one or more clips or clasps. Delivery tube 104 may also be rotatably engaged within port 103, allowing for 360 degree movement of delivery tube 104 in port 103. Delivery tube 104 may also be in close proximity with coupler 105 through any of a variety of manners that provides a gas-tight seal between delivery tube 104 and coupler 105. Coupler 105 may then be joined with any of a variety of sources of breathable gas, for example gas sources used in CPAP or BiPAP applications. Additionally, a source of breathable gas may be disposed in any location around mask 100 as delivery tube 104 and coupler 105 may be rotated 360 degrees to receive tubing, for example, that is connected to the source of breathable gas.

Delivery tube 104 may also have valve 118 disposed on its surface. Valve 118 may further include vent 119 and flap 121, and may also be held in place by connector 120, which is closed in an airtight seal when ventilation gas is being passed through delivery tube 104. Flap 121 is described further with respect to exemplary FIG. 3, however as shown in FIG. 1, vent 119 of valve 118 may be sealed by flap 121 when gas is delivered from a supply source. Alternatively, if there is no gas being delivered through delivery tube 104, the flap will open, allowing outside air to enter mask 100.

Ports 106 and 108 may also be disposed on outer body 102. Ports 106 and 108 may optionally be covered and sealed, as shown in FIG. 1. These ports may be used for any of a variety of functions, for example connecting to other sources of breathable gas or for the exhaust of waste gases, or, alternatively, connecting to any of a variety of monitors that are known to one having ordinary skill in the art. Additionally, ports 106 and 108 may have covers or seals that are attached to outer body 102. Thus ports 106 and 108 may be unsealed while their covers 107 and 109, respectively, are still attached to outer body 102, allowing for the ports to be quickly sealed and lowering the possibility of misplacing the covers for the ports. Posts 110 and 112 may also be disposed on outer body 102. These posts may be used as anchors or connection points for straps or a facial harness that can be used to secure mask 100 to the face of a wearer. Outer body 102 may also have a variety of exhaust ports, for example exhaust ports 114. The embodiment shown in FIG. 1 shows just one exemplary orientation of exhaust ports 114, however, and exhaust ports 114 may be disposed on any portion of outer body 114 and may be oriented in any fashion.

Facial interface cushion 116 may be removably connected to an inside perimeter of outer body 102. Cushion 116 may be formed out of any suitable material, for example silicone, PVC or polyurethane. Cushion 116 may be formed so as to provide a gas-tight seal between mask 100 and cushion 116 and also provide a gas-tight seal between cushion 116 and the face of a wearer. There may also be a chin portion 500 (extended portion) at a lower end of cushion and a chin flap 600 (single membrane) that may fit under the chin of a wearer. The a chin portion 500 may therefore serve to provide support for mask 100 on the face of a wearer, provide additional levels of comfort to a wearer and chin flap 600 provides additional sealing against the face, and particularly, the chin of a wearer. The chin portion 500 of cushion 116 does not limit the movement of a wearer, however. Instead a wearer can maintain the ability to open their mouth or perform adjustments of the mask on their face without compromising the gas-tight seal between mask 100 and their face provided by chin flap 600. Cushion 116 may also have two membranes on either side of the cushion, generating a gas-tight seal and coupling cushion 116 with outer body 102. The top and bottom portions of cushion 116 may only have one membrane. The one membrane may act to provide a seal between the face of a wearer while also increasing the pliability of cushion 116, thus improving the comfort level experience by a wearer.

Mask 100 may also have upper portion 122 that allows for mask 100 to be more properly secured to the face of a wearer and may act as a forehead brace or support structure. Upper portion 122 may have a variety of adjustable structures for the attachment of upper portion to outer body 102 and for adjusting the fitment of mask 100 to the face of wearer, the attachment of a harness or straps to secure mask 100 to the face and head of a wearer, and other structures to increase the comfort of a wearer.

Member 124 may have flanges 126 and 127 and eyelets 128 and 130. Member 124 may also be deformable, allowing for a wearer to modify the piece and adjust the fit of mask 100. Flanges 126 and 127 can act to secure member 124 to slide 135 and may also allow for some rotational movement of member 124 so as to provide a greater degree of adjustability. Eyelets 128 and 130 may act as anchors or receiving holes for straps, a harness or headgear that may be utilized to secure mask 100 to the face of a wearer. Slide 135 may be formed out of any material, for example plastic or metal. Additionally, slide 135 may be connected to member 124 and may accept link 134. Link 134 may be coupled to slide 135 through any of a variety of manners that can allow link 134 to be adjusted vertically. Link 134 may be formed so as to allow it to fit into receiving slot 132, thus securely coupling upper portion 122 with outer body 102 of mask 100. Clip or clasp 133 may be used to securely couple link 134 with receiving slot 132. Link 134 may also be formed so as to be shaped, deformable, bendable, pliable or malleable. In one exemplary embodiment, link 134 is formed out of a metal that can allow a wearer or any other person to adjust the shape or angle of link 134 and thus improving the fitment of upper portion 122 to the forehead of a wearer. In a further embodiment, link 134 may bent or angled at any degree so as to allow mask 100 to fit securely and comfortably against any of a variety of facial structures. The degrees of motion of link 134 are further shown with respect to FIGS. 4 and 5, below.

Link 134 may also have a variety of holes 136. Holes 136 may be used when adjusting upper portion 122 vertically. For example, if a wearer wants to alter the height of upper portion 122 on their forehead, slide 135 may be moved up, allowing for a different hole 136 on link 134 to be joined to slide 135 via clasp 138. Additionally, the lower portion of link 134 may have a series of holes 136 that allow for link 134 to be joined to outer body 102 via clip or clasp 133 in receiving slot 132. Further, link 134 may include slot 139, which may be disposed on the link and can be used to create a weak area on link 134, thus increasing the ease with which link 134 may be deformed or molded. Link 134 may be deformed or molded by any party, such as a wearer seeking to improve the fit of the ventilation mask on their face. In a further exemplary embodiment, clasp 138 may include a lever. The lever may be operated in any of a variety of manners, for example a user operating the lever with their thumb or any other finger. Thus a wearer could push up on clasp 138, separating it from link 134, and moving upper portion 122 either upwards or downwards in a manner requiring little effort on the part of the wearer. Upon releasing clasp 138, clasp 138 would engage the desired hole 136 on link 134, locking upper portion 122 in the desired location for the wearer. In yet another exemplary embodiment, upper portion 122 may be formed as a single part, incorporating member 124, link 134 and slide 135 into a single piece.

Upper portion 122 may also incorporate cushion 140. Cushion 140 may be formed out of any soft or comfortable material, such as rubber, silicone, foam or any other suitable material known to one of ordinary skill in the art. Cushion 140 may be disposed on an inside portion of member 124 and can be applied to the forehead of a wearer. Additionally, cushion 140 should be oriented so that parts of upper portion 122 that may cause discomfort or may interfere with the desired use of mask 100 either do not contact or adversely interfere with the use of mask 100.

Figure 2:
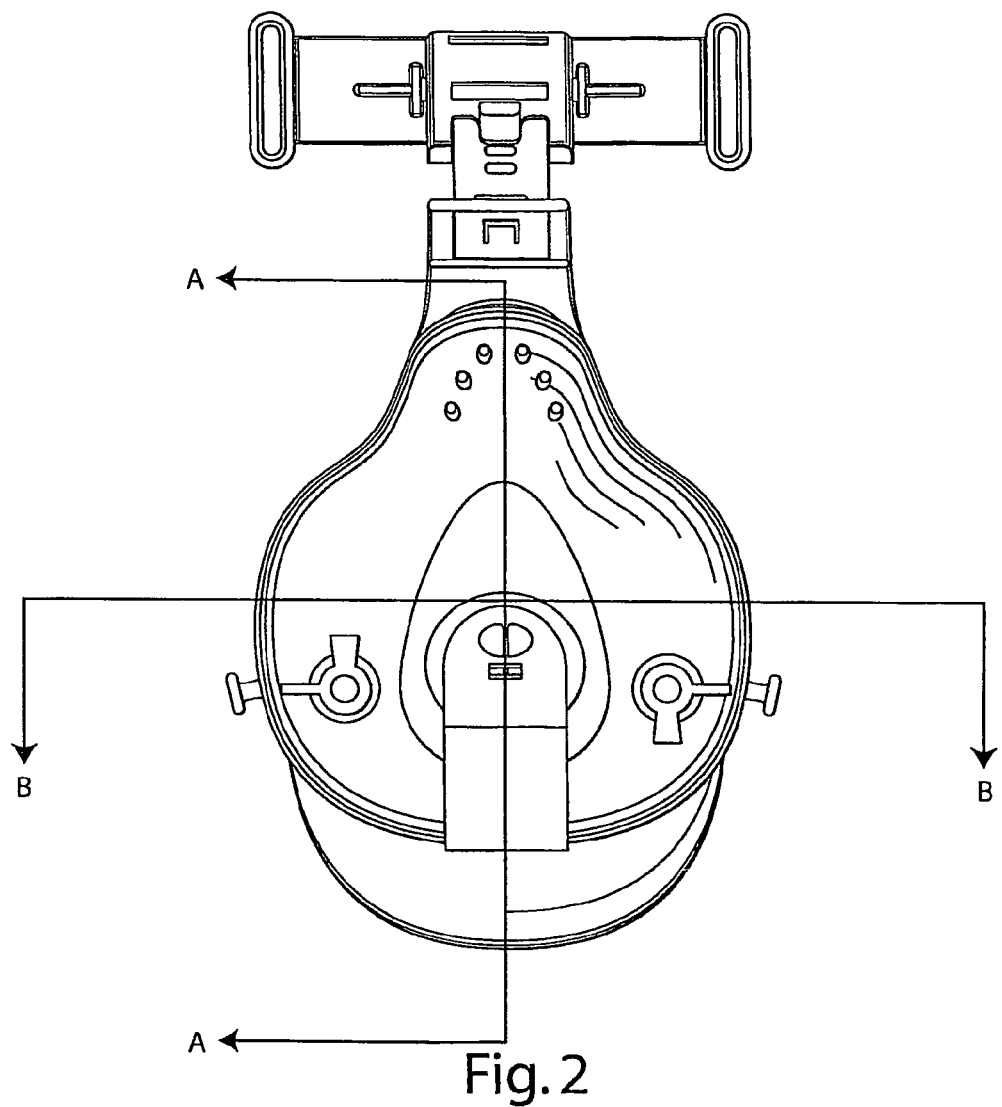
FIG. 2 shows an exemplary front view of a ventilation mask.

FIG. 2 shows an exemplary front view of a ventilation mask. Here, the chin portion 500 of cushion 116 can be seen as extending below outer body 102 so as to fit under the chin of a wearer. Additionally, vertical adjustment of slide 134, as well as bending slide 134 fore and aft, may also act to adjust the location or placement of the chin portion 500 of cushion 116. Further, in this exemplary view, posts 110 and 112 are shown as projecting from opposite sides of outer body 102. Posts 110 and 112 may optionally be larger or smaller, or may have different shapes or structures, depending on the type of headgear, harness or straps used to secure mask 100 to the face of a wearer. Posts 110 and 112 may also optionally be located on any other portion of mask 100.

Ports 106 and 108 are shown as sealed by covers 107 and 109, respectively, in the exemplary embodiment shown in FIG. 2. The covers for ports 106 and 108 may be of any size, shape or design that is capable of providing a gas-tight seal.

Figure 3:
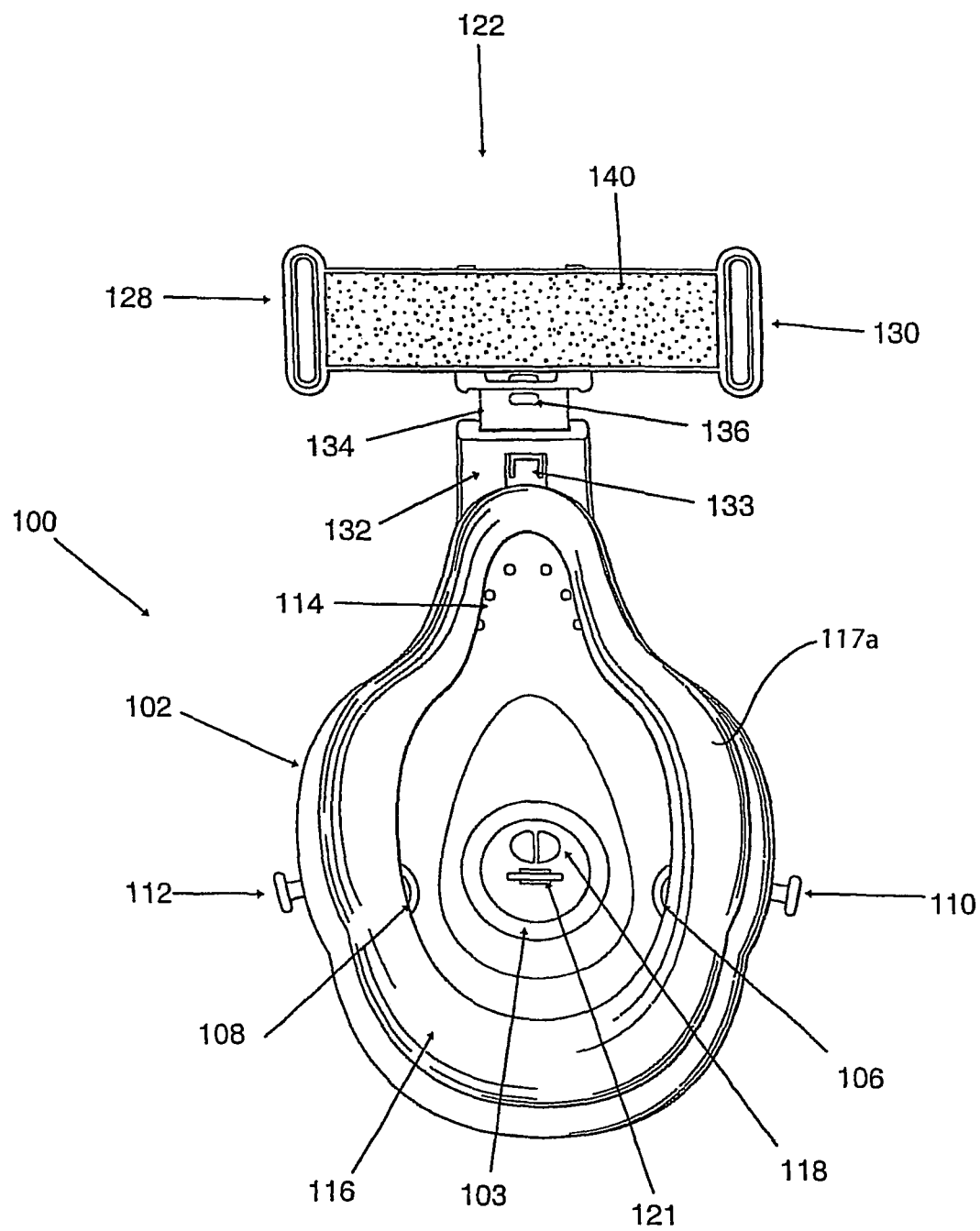
FIG. 3 shows an exemplary rear view of a ventilation mask.
Figure 8:
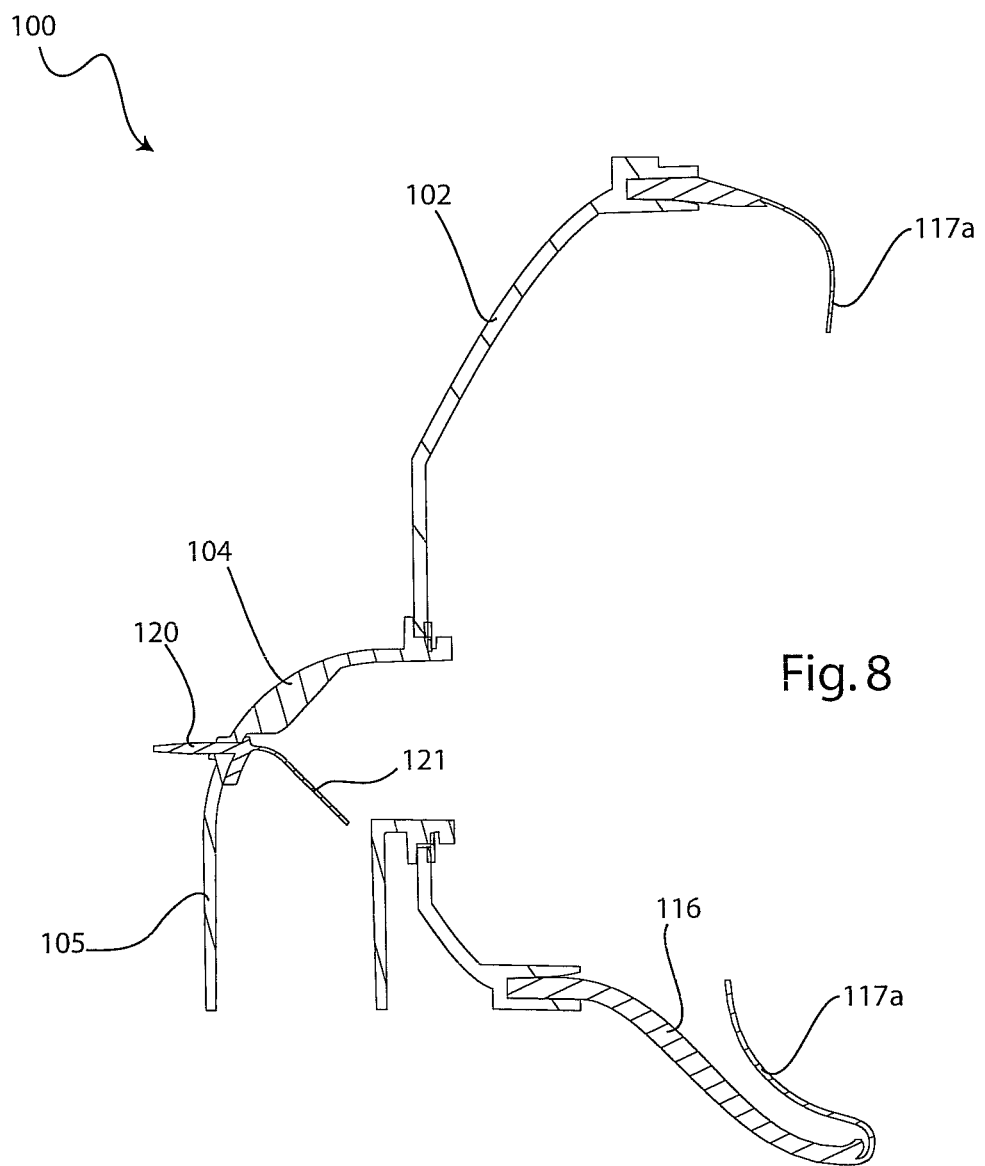
FIG. 8 shows an exemplary cross-sectional side view of a ventilation mask.
Figure 9:
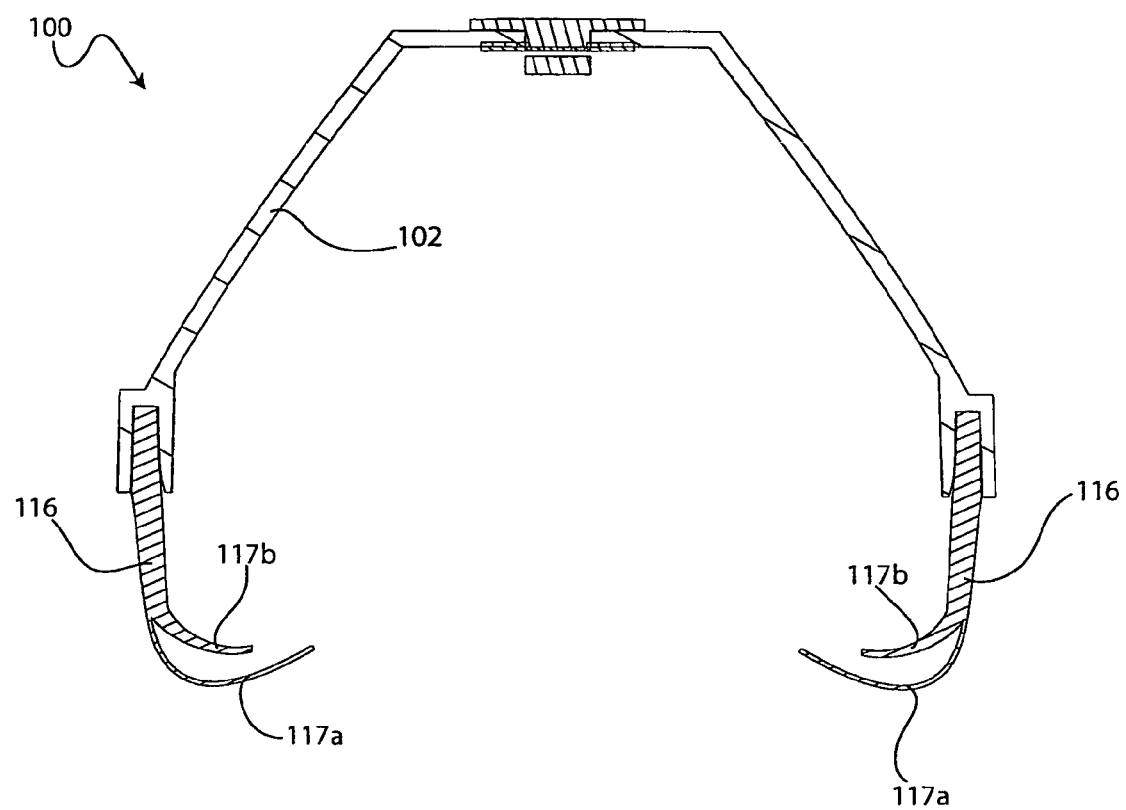
FIG. 9 shows an exemplary cross-sectional top view of a ventilation mask.

FIG. 3 shows an exemplary rear view of a ventilation mask. FIG. 8 is a cross-sectional side view of ventilation mask 100 taken along line A-A as shown in FIG. 2. FIG. 9 is a cross-sectional top view of ventilation mask 100 taken along line B-B as shown in FIG. 2 From this view, the shape of facial interface cushion 116 can be seen as having a narrow upper portion and a wide center portion that tapers in slightly towards the lower portion. The shape of cushion 116 is such that it conforms to the contours of the face of a wearer. Variations of the shape of the removably attached cushion may, however, be used to better suit the facial structure of a particular wearer. Additionally, the cushion may be adjusted or altered to provide for better comfort on the face of a wearer or to provide for better sealing against the face of a wearer. Cushion 116 may also utilize two or more membranes 117a and 117b on its interior portions, as shown in FIG. 9. Moreover, cushion 116 utilizes two membranes 117a and 117b on a first side and a second side of cushion 116. Two membranes 117a and 117b may act to provide a gas tight seal against the face of a wearer. The narrow top portion and chin portion 500 of cushion 116 may only have membrane 117a, however, which can provide gas-tight seals against the face of a wearer, as shown in FIG. 8. In one exemplary embodiment, the narrow top portion of cushion 116 may have membrane 117a that comfortably seals against the nose of a wearer. In a further exemplary embodiment, the chin portion 500 of cushion 116 may have membrane 117a chin flap 600 that comfortably seals against the chin of a wearer. In another exemplary embodiment chin flap 600 and membrane 117a ma be a single membrane.

As shown in FIG. 8, in one embodiment, chin flap 600 may be coupled to a distal end of chin portion 500 and extend away therefrom. Chin flap 600 may be positioned adjacent chin portion 500 such that chin flap 600 may be oriented substantially parallel to chin portion 500. Chin flap 600 may comfortably seal against the chin of a wearer.

Figure 4:
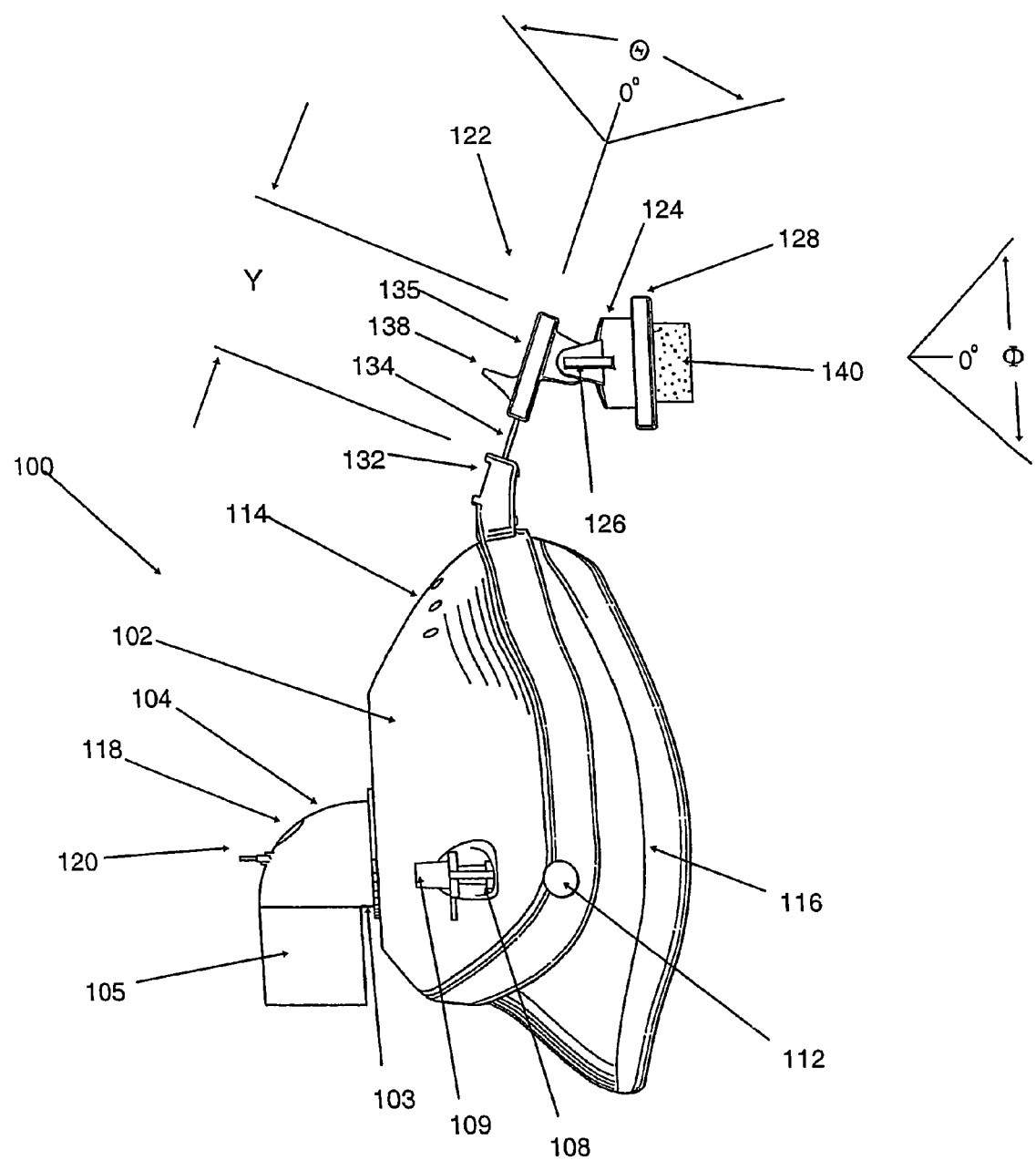
FIG. 4 shows an exemplary side view of a ventilation mask.

FIG. 4 shows an exemplary side view of a ventilation mask. Facial interface cushion 116 is shown having an extended lower portion that may act to seal against the chin of a wearer. In other exemplary embodiments of the invention, the lower extended portion of cushion 116 may be formed in a variety of different manners, such as being lower, wider or any other shape that may more comfortably seal against the chin of a wearer.

FIG. 4 shows an exemplary side view of a ventilation mask. Facial interface cushion 116 is shown having chin portion 500 and chin flap 600 that may act to seal against the chin of a wearer. In other exemplary embodiments of the invention, the chin portion of cushion 116 may be formed in a variety of different manners, such as being lower, wider or any other shape that may more comfortably seal against the chin of a wearer.

FIG. 4 also shows an exemplary side view of upper portion 122 of mask 100. From this exemplary view, it is shown that link 134 may be bent or molded to adjust upper portion 122 for the proper level of comfort and sealing. In one exemplary embodiment shown in FIG. 4, link 134 may be bent at any angle Θ, which may be in the range of 90 degrees in either direction from the zero degree axis. Further, link 134 may be infinitely adjustable within the range of 90 degrees in either direction from the zero degree axis. Additionally, flange 126 is shown, which, along with flange 127, may be hinged and thus allow for hinged movement of member 124. Thus, member 124 may be a hinging member capable of being adjusted to any desirable angle. In one exemplary embodiment shown in FIG. 4, hinging member 124 may be bent at any angle Φ, which may be in the range of 90 degrees in either direction from zero degrees. Hinging member 124 may also be infinitely adjustable within the range of 90 degrees in either direction from the zero degree axis. Further, cushion 140 is shown as mounted on the inside portion of member 124. Cushion 140 may utilize any size cushion that may optionally cover more or less area on the inside of member 124 and may extend from member 124 by any of a variety of lengths, so as to ensure the comfort of a wearer of mask 100.

In yet another embodiment shown in FIG. 4, upper portion 122 may be adjusted a distance Y through the use of slide 135 and link 134. In one exemplary embodiment of the invention, upper portion 122 may be adjusted a distance between zero inches and 3". In one embodiment, upper portion 122 is infinitely adjustable within the range of zero inches to 3". In another embodiment, upper portion 122 may be adjusted in increments of about 0.16".

Figure 5:
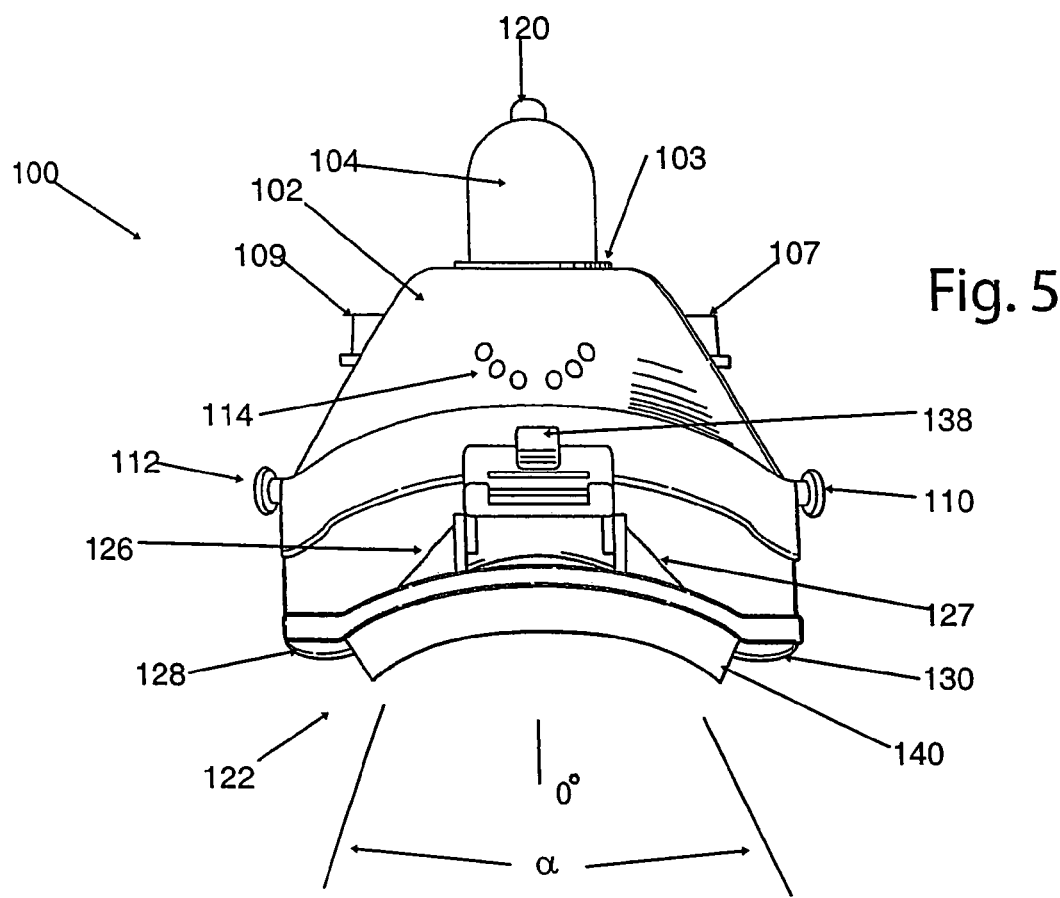
FIG. 5 shows an exemplary top view of a ventilation mask.

FIG. 5 is an exemplary top view of a ventilation mask. In this exemplary embodiment, cushion 140 is shown as being curved. In other embodiments, cushion 140 may be adjustable, removable or replaceable. Thus, cushion 140 may be flat or disposed at an angle that best suits a particular wearer of mask 100. Additionally, exhaust ports 114 are shown on an upper portion of outer body 102. As mentioned previously, these ports may be of any size or shape and may be located anywhere on outer body 102. In another exemplary embodiment shown in FIG. 5, link 134 may be bent laterally at any angle α, which may be in the range of 45 degrees in either direction from zero degrees. Link 134 may further be adjusted infinitely within the range of 45 degrees in either direction from zero degrees.

Figure 6:
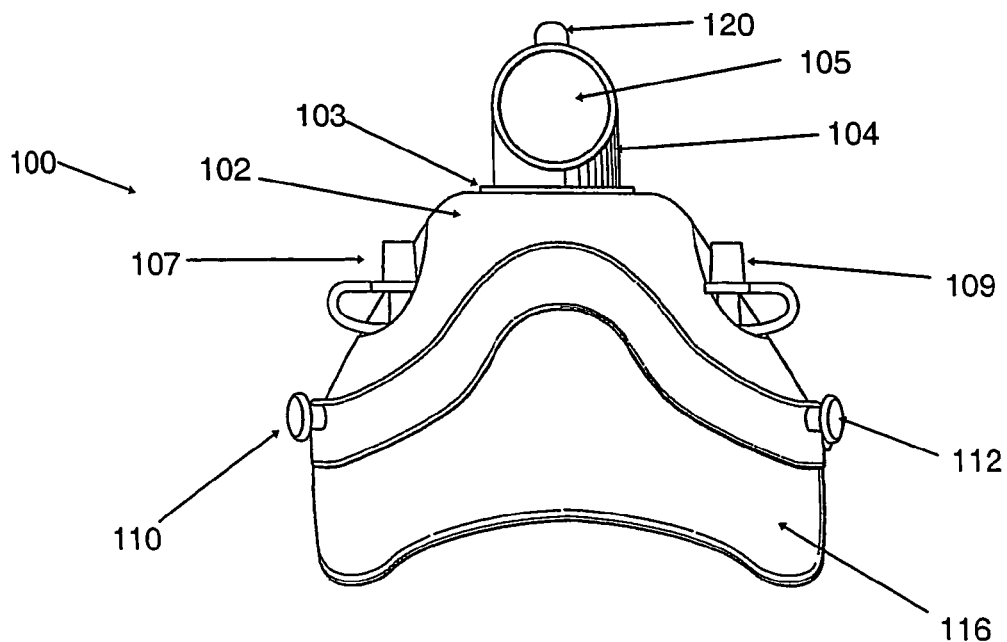
FIG. 6 shows an exemplary bottom view of a ventilation mask.

FIG. 6 is an exemplary bottom view of a ventilation mask. Again, facial interface cushion 116 is shown as having chin portion 500 and chin flap 600 for sealing against the chin of a wearer. In other embodiments, the chin portion 500 of cushion 116 may extend a greater or lesser distance and may incorporate additional cushioning that increases the comfort of the wearer while chin flap 600 keeps a gas tight seal between the face of the wearer and mask 100. Further, cushion 116 may be coupled to outer body 102 of mask 100 in any manner that maintains a gas-tight seal between cushion 116 and mask 100. In one non-limiting exemplary embodiment shown in FIG. 6, cushion 116 and mask 100 are coupled using a combination of friction between cushion 116 and mask 100 as well as a tongue-in-groove style of fixing the cushion to the mask.

Figure 7:
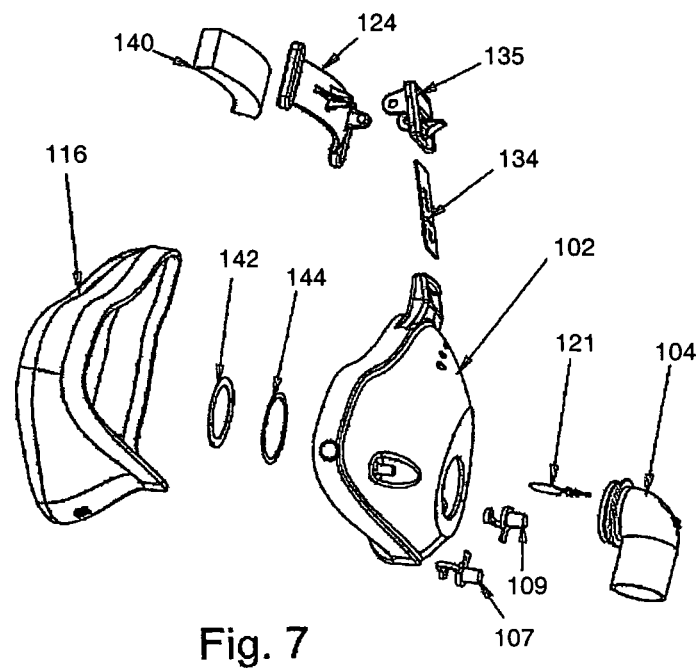
FIG. 7 shows an exemplary exploded view of a ventilation mask.

FIG. 7 is an exemplary exploded view of a ventilation mask. This figure shows. Included in this exemplary figure are clip ring 142 and bearing ring 144. Clip ring 142 and bearing ring 144 may be used to couple delivery tube 118 with outer body 102 while allowing delivery tube 118 to rotate inside port 103. Additionally, seals 107 and 109 are shown as detached and not cover ports 106 and 108, respectively.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed:

1. A ventilation mask, comprising:
    an outer body including at least one gas entry port to be connected to a source of breathable gas;
    a cushion connected to the outer body about a perimeter, the cushion forming a gas-tight seal with the outer body, and further having:
        at least one interior membrane;
        a chin portion that extends below the outer body;
        and a chin flap coupled to a distal end of the chin portion and extending toward the at least one gas entry port such that the chin flap is positioned adjacent the chin portion and oriented substantially parallel thereto, wherein the chin flap facilitates providing chin support and has a single surface that facilitates providing a seal against a face and under the chin of a wearer; and
    an upper portion adjustably secured to the outer body and having a forehead cushion.

2. The ventilation mask of claim 1, wherein the upper portion is formed as one piece and that can be adjusted vertically.

3. The ventilation mask of claim 1, further comprising a deformable link connecting the upper portion to the outer body.

4. The ventilation mask of claim 3, further comprising a slot in the deformable link configured to facilitate deformation of the link.

5. The ventilation mask of claim 3, further comprising at least one hole in the deformable link to facilitate securing the deformable link to the upper portion.

6. The ventilation mask of claim 1, wherein the upper portion can be adjusted fore and aft.

7. The ventilation mask of claim 6, wherein the upper portion has a 180 degree range of fore and aft motion.

8. The ventilation mask of claim 1, wherein the upper portion can be adjusted laterally.

9. The ventilation mask of claim 8, wherein the upper portion has a 90 degree range of lateral motion.

10. The ventilation mask of claim 1, wherein the upper portion can be adjusted vertically.

11. The ventilation mask of claim 10, wherein the upper portion has a range of motion of at least 0.100".

12. The ventilation mask of claim 10, wherein the upper portion is adjusted through the use of a lever.

13. The ventilation mask of claim 1, wherein the angle of the upper portion can be adjusted.

14. The ventilation mask of claim 13, wherein the upper portion has a 180 degree range of motion.

15. The ventilation mask of claim 1, wherein the chin portion of the cushion extends below the perimeter.

16. The ventilation mask of claim 1, wherein the at least one membrane comprises two membranes that provide a seal between the cushion and a wearer of the mask.

17. The ventilation mask of claim 1, wherein the cushion has at least two membranes on a first side of the cushion and at least two membranes on a second side of the cushion.

18. The ventilation mask of claim 1, wherein the cushion has one membrane at the top of the cushion and one membrane at the bottom of the cushion.

19. The ventilation mask of claim 1, wherein a gas delivery tube is rotatably engaged in the at least one gas entry port.

20. A ventilation mask, comprising:
    an outer body;
    a gas delivery tube;
    a gas delivery port;
    a cushioned facial interface connected to the outer body about a perimeter, comprising:
        at least one interior membrane,
        a chin portion that extends below the outer body; and
        a chin flap coupled to a distal end of the chin portion and extending toward the gas delivery port such that the chin flap is positioned adjacent the chin portion and oriented substantially parallel thereto, wherein the chin flap facilitates providing chin support and has a single surface that facilitates providing a seal against a face and under the chin of a wearer;
    a support structure; and
    an adjustable upper portion having a forehead cushion; the gas delivery tube rotatably connected to the outer body at the gas delivery port and creating a seal therebetween, the cushioned facial interface removably connected to the outer body and creating a seal therebetween, and the adjustable upper portion connected to the support structure.

21. The ventilation mask of claim 20, wherein the adjustable upper portion may be deformed to adjust the fit of the support structure.

22. The ventilation mask of claim 20, wherein the adjustable upper portion is adjustable fore, aft, vertically, horizontally and rotationally.

23. The ventilation mask of claim 20, wherein the cushioned facial interface has an extended lower portion.

24. The ventilation mask of claim 20, wherein the cushioned facial interface has a first membrane on a top portion of the cushioned facial interface, a first membrane on the bottom portion of the cushioned facial interface, and a first membrane and a second membrane on a first side of the cushioned facial interface and a first membrane and a second membrane on a second side of the cushioned facial interface.

25. The ventilation interface of claim 20, further comprising at least one post for the attachment of headgear.

26. The ventilation interface of claim 20, wherein the cushioned facial interface is formed out of silicone.

27. The ventilation interface of claim 20, wherein the outer body has at least one exhaust port.

28. A cushion for a ventilation mask, comprising:
    a first side having a first and second membrane;
    a second side having a first and second membrane;
    a top portion having only a first membrane; and
    a chin portion and a chin flap coupled to a distal end of the chin portion; the first side, second side, top portion and chin portion forming a gas tight seal between the cushion and a ventilation mask wherein the chin flap extends outwards from the cushion such that the chin flap is positioned adjacent the chin portion and oriented substantially parallel to the chin portion to facilitate providing support for the ventilation mask and wherein the chin flap has a single surface to facilitate providing a seal against a face and under a chin of a wearer.

29. The cushion of claim 28, wherein the cushion forms a gas tight seal between the cushion and the face of the wearer.

* * * * *